(12) United States Patent
Rainey

(10) Patent No.: US 7,909,675 B1
(45) Date of Patent: Mar. 22, 2011

(54) GARMENT WITH BREAST IMPLANT STABILIZERS

(75) Inventor: Russell Rainey, Atlanta, GA (US)

(73) Assignee: Rainey Apparel Manufacturing, Inc., Atlanta, GA (US)

( * ) Notice: Subject to any disclaimer, the term of this patent is extended or adjusted under 35 U.S.C. 154(b) by 895 days.

(21) Appl. No.: 11/785,908

(22) Filed: Apr. 20, 2007

Related U.S. Application Data

(63) Continuation-in-part of application No. 11/589,863, filed on Oct. 31, 2006, now abandoned.

(60) Provisional application No. 60/731,499, filed on Oct. 31, 2005.

(51) Int. Cl.
*A41C 3/00* (2006.01)

(52) U.S. Cl. .......................... 450/59; 450/85

(58) Field of Classification Search ........... 450/1, 2, 450/7, 8, 9, 10, 11, 14–17, 23, 26, 28, 30–33, 450/59–62, 74–76, 85
See application file for complete search history.

(56) References Cited

U.S. PATENT DOCUMENTS

| | | | |
|---|---|---|---|
| 1,167,741 A | | 1/1916 | Clarke |
| 1,448,639 A | * | 3/1923 | Reece ............... 450/59 |
| 1,466,598 A | | 8/1923 | Panes |
| 1,584,525 A | * | 5/1926 | Freeman ............. 450/62 |
| 1,904,644 A | * | 4/1933 | Le May ............. 450/59 |
| 2,427,402 A | * | 9/1947 | Gluckin ............. 450/59 |
| 2,454,153 A | * | 11/1948 | Glick ............... 450/36 |
| 2,456,695 A | * | 12/1948 | Gluckin ............. 450/59 |
| 2,468,621 A | * | 4/1949 | Glick ............... 450/53 |
| 2,475,624 A | | 7/1949 | Laszlo |
| 2,484,440 A | * | 10/1949 | Witkower ............ 450/59 |
| 2,487,210 A | * | 11/1949 | Barco ............... 450/62 |
| 2,553,225 A | * | 5/1951 | Weaver et al. ........ 450/59 |
| 2,574,962 A | * | 11/1951 | Curran .............. 450/48 |
| 2,734,193 A | | 2/1956 | Croxall |
| 3,332,426 A | | 7/1967 | Kaplan |
| 3,419,895 A | | 12/1968 | Stephensen |
| 3,491,762 A | | 1/1970 | Simonsen |
| 3,628,539 A | | 12/1971 | Fredricks |
| 3,642,009 A | | 2/1972 | Nobbs |
| 3,710,800 A | | 1/1973 | Carey |
| 3,769,987 A | | 11/1973 | Markowitz |
| 4,369,792 A | | 1/1983 | Miller |
| 4,412,357 A | | 11/1983 | Mincher |
| 4,444,191 A | | 4/1984 | Harned |
| 4,741,719 A | | 5/1988 | Wirth |
| 5,037,348 A | | 8/1991 | Farino |
| 5,098,331 A | | 3/1992 | Corrado |
| 5,152,741 A | | 10/1992 | Farnio |
| 5,158,541 A | | 10/1992 | McCurley |
| 5,537,690 A | | 7/1996 | Johnson |

(Continued)

*Primary Examiner* — Gloria Hale
(74) *Attorney, Agent, or Firm* — Jacobson Holman, PLLC

(57) ABSTRACT

A breast garment for stabilizing breast implants includes a body surrounding the wearer's mid to upper torso, left and right built-in implant stabilizers positioned at the front of the body for applying medium to firm downward and lateral pressure on a wearer's breasts, and an adjustable front closure provided at the front edges of the body for making the body tighter or loose for adjusting the amount of downward and lateral pressure. The implant stabilizers have top, bottom, front, and back edges, with a cut-out in the front edge shaped to permit the areole and surrounding area of the breast to protrude therethrough. The body and the implant stabilizers are made of a stretch compressive fabric.

29 Claims, 9 Drawing Sheets

U.S. PATENT DOCUMENTS

| | | |
|---|---|---|
| 5,897,422 A | 4/1999 | McGee |
| 5,968,003 A | 10/1999 | Sisson |
| 6,055,668 A | 5/2000 | Gros et al. |
| 6,113,460 A | 9/2000 | McKeown |
| 6,135,975 A | 10/2000 | Johnstone |
| 6,168,498 B1 | 1/2001 | Wagner |
| D446,629 S | 8/2001 | Swanger |
| 6,296,618 B1 | 10/2001 | Gaber |
| 6,390,885 B1 | 5/2002 | Brooks |
| 6,572,437 B1 | 6/2003 | Waitz |
| 6,746,306 B2 | 6/2004 | Brothers |
| 6,755,717 B2 | 6/2004 | Smith |
| 6,786,798 B1 | 9/2004 | Gendel |
| 6,860,789 B2 | 3/2005 | Bell et al. |
| D503,509 S | 4/2005 | Bell et al. |
| 6,936,021 B1 | 8/2005 | Smith |
| 6,953,380 B2 | 10/2005 | Brothers |
| 7,435,155 B2 * | 10/2008 | Reinisch et al. ............ 450/59 |
| 7,666,058 B2 * | 2/2010 | Smith ............................ 450/8 |
| 2002/0022432 A1 | 2/2002 | Magrone |
| 2003/0166375 A1 | 9/2003 | Noel et al. |
| 2005/0009445 A1 | 1/2005 | Bell et al. |
| 2005/0154341 A1 | 7/2005 | Wadstrom |

* cited by examiner

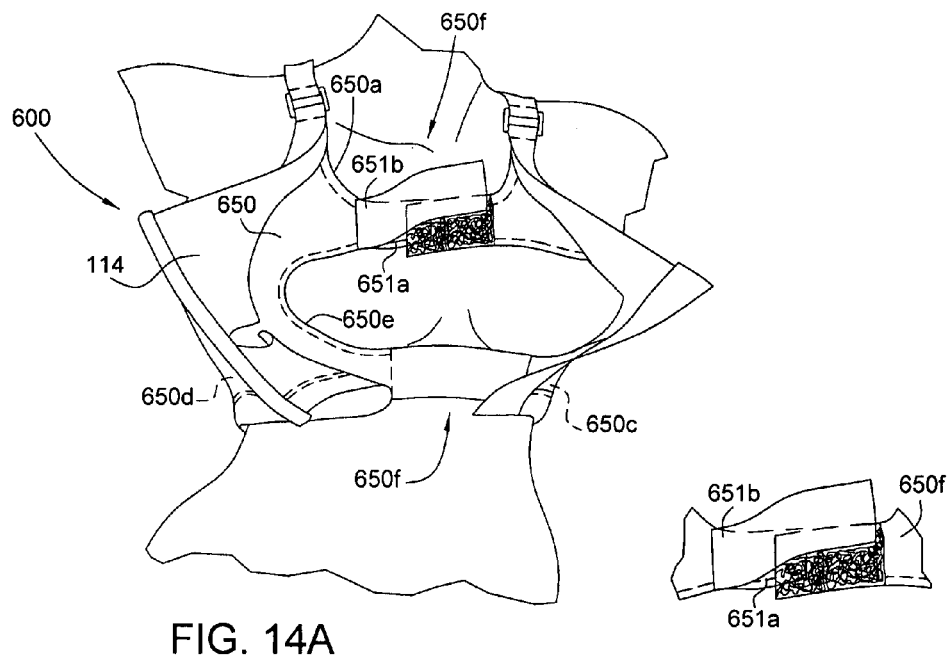
FIG. 14A
FIG. 14C
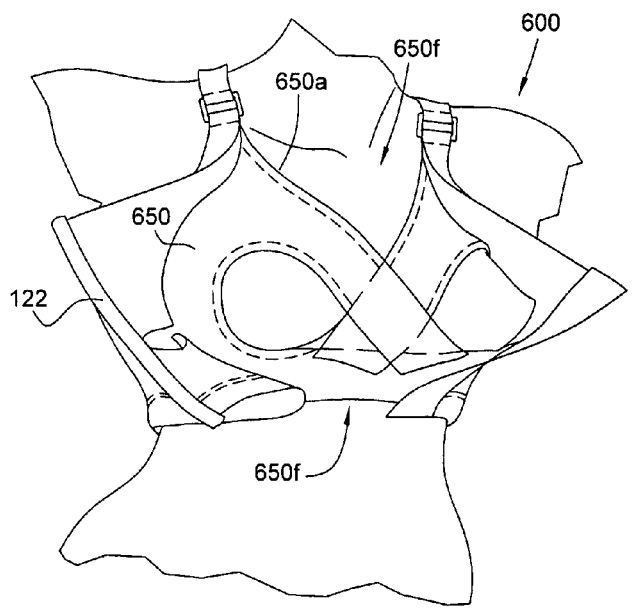
FIG. 14B

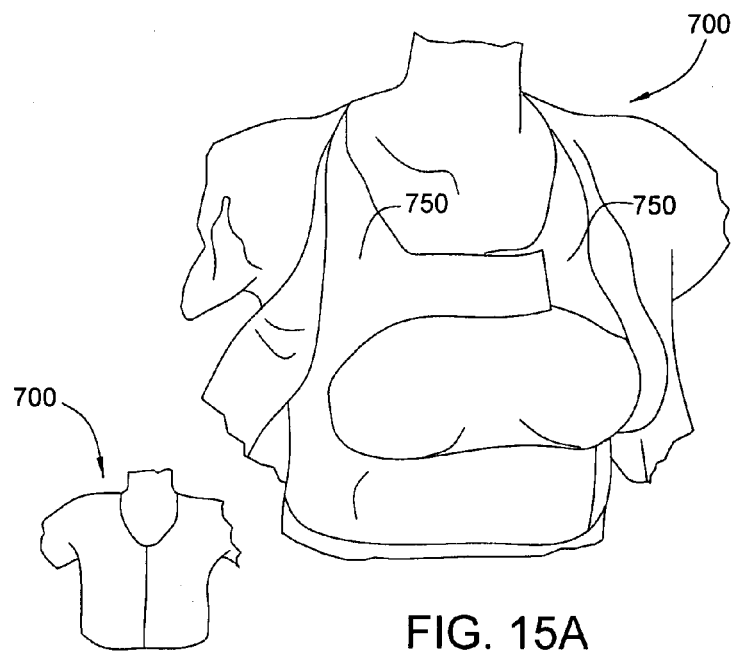
FIG. 15A
FIG. 15C
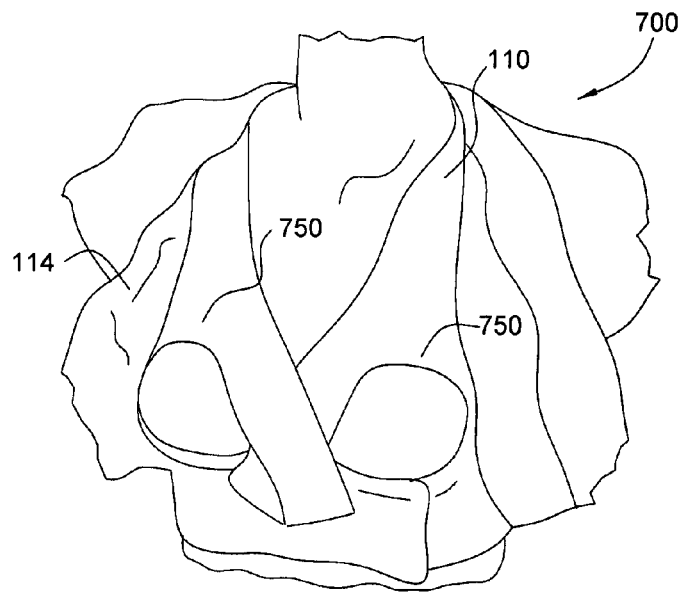
FIG. 15B

GARMENT WITH BREAST IMPLANT STABILIZERS

CROSS-REFERENCE TO RELATED APPLICATIONS

The present patent application is a continuation-in-part of U.S. patent application Ser. No. 11/589,863, filed Oct. 31, 2006 now abandoned, which is based on, and claims priority from, U.S. provisional Application No. 60/731,499, filed Oct. 31, 2005, which is incorporated herein by reference in its entirety.

BACKGROUND OF THE INVENTION

1. Field of the Invention

The present invention relates to garments for post-operative application. More specifically, the invention relates to a garment for stabilizing breast implants following their surgical placement in breast augmentation or reconstructive procedures.

2. Related Art

Specialized breast garments (for example, Style Nos. BL, BS, and A1 (formerly Style Nos. WAS-70, WAS-71, and WSB-72, respectively) sold by Rainey Compression Essentials of Atlanta, Ga.) are used for breast support after augmentation or breast lift procedures to generally aid in the healing transformation of patients. These breast garments may be in the form of bras or vests, and are usually made from a strong, lightweight, breathable fabric that is latex free and provides a comfortable feel against the wearer's skin.

However, these breast garments do not themselves provide for implant positioning and stabilization. To achieve implant positioning and stabilization, as well as post-operative comfort, it has been necessary for the patient to wear a separate adjustable elastic bandeau that surrounds the breasts and extends around the mid-torso below the breasts (such as Style No. WP (formerly Style No. WBB-75) sold by Rainey Compression Essentials), or an adjustable elastic band that extends around the upper torso above the breasts (such as Style No. P-75 (formerly Style No. WPB-77), also sold by Rainey Compression Essentials).

Other garments provide post-surgical compression as well as support for the breasts, but do not provide for the positioning and stabilization of breast implants. For example, U.S. Pat. No. 6,786,798 and published patent appl. No. 2004/0185748 (Gendel) disclose a bra to be worn after breast surgery, with support panels 42 each of which has an "L" shape so as to extend downwardly from the axilla and under the breast. U.S. Pat. No. 6,135,975 (Johnstone) discloses a bra-style surgical chest dressing having an adjustable bodice front hook and loop closure, strap front adjustable hook and loop closures, and non-stretchable panels biasing the side and breast tissue. U.S. Pat. No. 5,152,741 (Farnio) discloses a similar bra-style surgical chest dressing, except that the biasing panels are stretchable.

U.S. Pat. No. 5,037,348 (Farino) discloses a therapeutic bra for breasts having implants, having elastic strips of material attached to the upper marginal edges of the cups and to the midriff band to prevent movement or distortion of the breast implants. However, Farino's therapeutic bra is not configured to otherwise generally aid in the healing transformation of patients.

It is to the solution of these and other problems that the present invention is directed.

SUMMARY OF THE INVENTION

It is accordingly a primary object of the present invention to provide a single garment for use following the insertion of breast implants (for example, in breast augmentation or breast lift procedures) that generally aids in the healing transformation of patients, while also achieving implant positioning and stabilization.

It is another object of the present invention to provide a single garment for use following the surgical placement of breast implants, while achieving implant positioning and stabilization by helping to prevent upward and lateral movement of the implants.

These and other objects are achieved by the provision of a breast garment for stabilizing breast implants following their surgical placement during breast augmentation or reconstructive procedures, comprising a body surrounding the wearer's mid to upper torso, stabilizing means for applying medium to firm downward and lateral pressure on a wearer's breasts to help muscle tissue relax and accept breast implants in their new position, for providing downward pressure on a wearer's breasts to prevent upward movement of breast implants, and for providing pressure on a wearer's breasts to prevent lateral movement of implants, and tightness adjusting means for adjusting the tightness of the garment around the mid to upper torso of the wearer.

The body has a back panel, a front, and a bottom edge and an elastic band at the bottom edge of the body for providing proper fit around the wearer's midriff. The back panel has left and right sides, and left and right front panels extending forwardly from the left and right sides of the back panel, and the left and right front panels having respective, opposing front edges. The body is made of a knitted tricot stretch compressive fabric;

In one aspect of the invention, the tightness adjusting means comprises a front closure provided at the front edges of the left and right front panels, the front closure being adjustable to make the body tighter or looser.

In another aspect of the invention, the stabilizing means comprise left and right built-in implant stabilizers positioned at the front of the body, wherein the left and right built-in implant stabilizers are made of a stretch compressive fabric, and the left and right stabilizers have top, bottom, front, and back edges, with a cut-out in the front edge shaped to permit the areole and surrounding area of the breast to protrude therethrough.

The stabilizing means can be located on the inside or the outside of the body, and can be provided with one or more adjustable stabilizer closures.

Other objects, features, and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIG. 14A is a front views of a sixth embodiment of the garment with breast implant stabilizers in accordance with the invention, with the upper stabilizer closures fastened in a first position.

FIG. 14B is a front perspective view of the sixth embodiment of the garment with breast implant stabilizers in accordance with the invention, with the upper stabilizer closures fastened in a second position.

FIG. 14C is an enlarged view of the upper stabilizer closures fastened in the first position.

FIG. 15A is a front perspective view of the seventh embodiment of the garment with breast implant stabilizers in accordance with the invention, with the upper stabilizer closures fastened in a first position.

FIG. 15B is a front perspective view of the seventh embodiment of the garment with breast implant stabilizers in accordance with the invention, with the upper stabilizer closures fastened in a second position.

FIG. 15C is a front perspective view of the seventh embodiment of the garment with breast implant stabilizers in accordance with the invention, with the front closure closed.

DETAILED DESCRIPTION OF THE PREFERRED EMBODIMENTS

Figure 1:
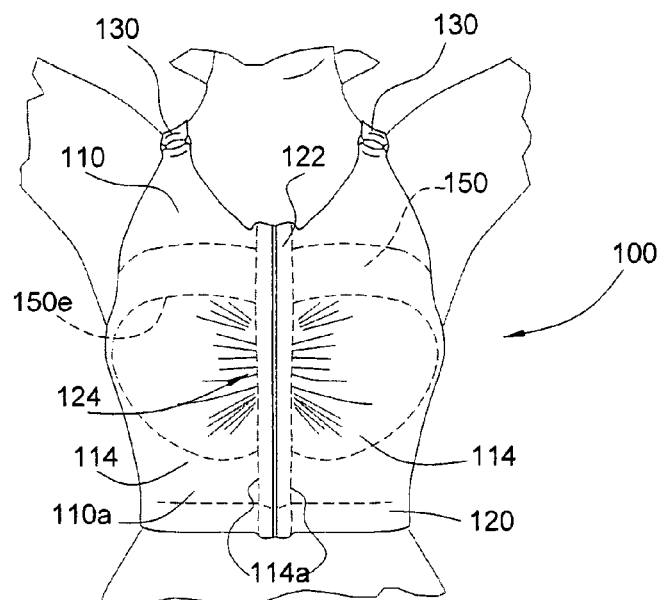
FIG. 1 is a front view of a first embodiment of the garment with breast implant stabilizers in accordance with the invention.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

As used herein, directional terms including, but not limited to, "left" and "right," "front" and "back," and "top" and "bottom" are used with reference to the wearer of a breast garment in accordance with the present invention, unless as otherwise noted.

Referring now to FIGS. 1-6, there is shown a breast garment 100 in accordance with a first embodiment of the invention for stabilizing breast implants following their surgical placement during breast augmentation or reconstructive procedures.

The breast garment 100 comprises a body 110 that surrounds the wearer's mid to upper torso and left and right built-in implant stabilizers 150 (best seen in FIG. 4) positioned on the inside of the body 110 at the front. By "built-in," it is meant that the implant stabilizers 150 form a part of the garment 100, and are not detachable therefrom. The body 110 and the implant stabilizers 150 are both made of a stretch compressive fabric (for example, knitted tricot), preferably in a nylon/lycra blend.

The body 110 includes a back panel 112 having left and right sides 112a, and left and right front panels 114 extending forwardly from the left and right sides of the back panel 112. The left and right front panels 114 have respective, opposing front edges 114a. The left and right front panels 114 can be joined to the back panel 112 by side seams 116, or can be unitary with the back panel 112. An elastic band 120 at the bottom edge 110a of the body 110 provides proper fit around the wearer's midriff. The elastic band 120 can be sewn to the body 110 adjacent the bottom edge 110a of the body 110 or can be encased in a casing along the bottom edge 110a of the body 110, in conventional fashion.

Figure 3:
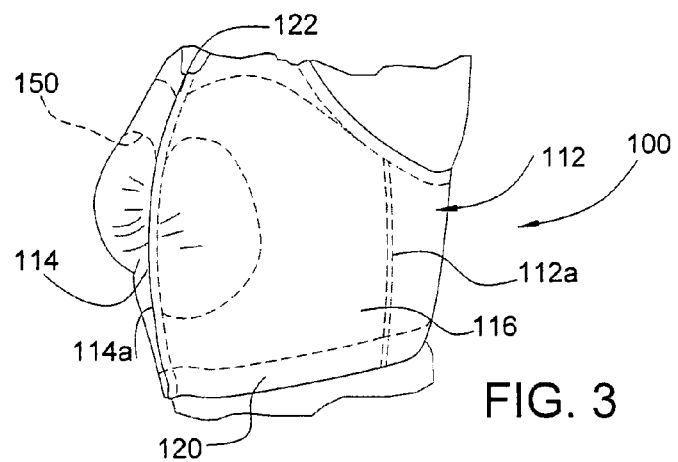
FIG. 3 is a side perspective view of the garment of FIG. 1.
Figure 3A:
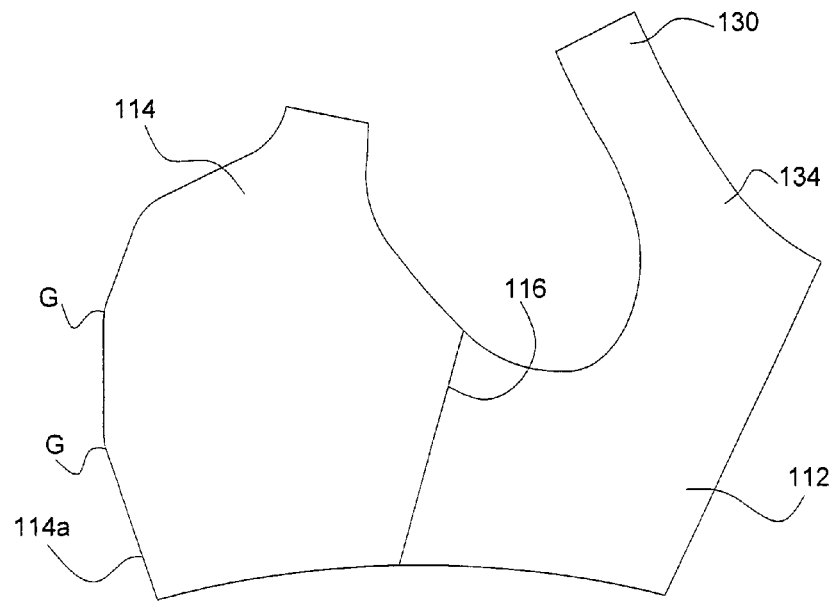
FIG. 3A is an elevational view of a front panel and a side of the back panel prior to finishing and assembly into the garment of FIG. 1, in which the front panel and the side of the back panel are formed as separate pieces.
Figure 3B:
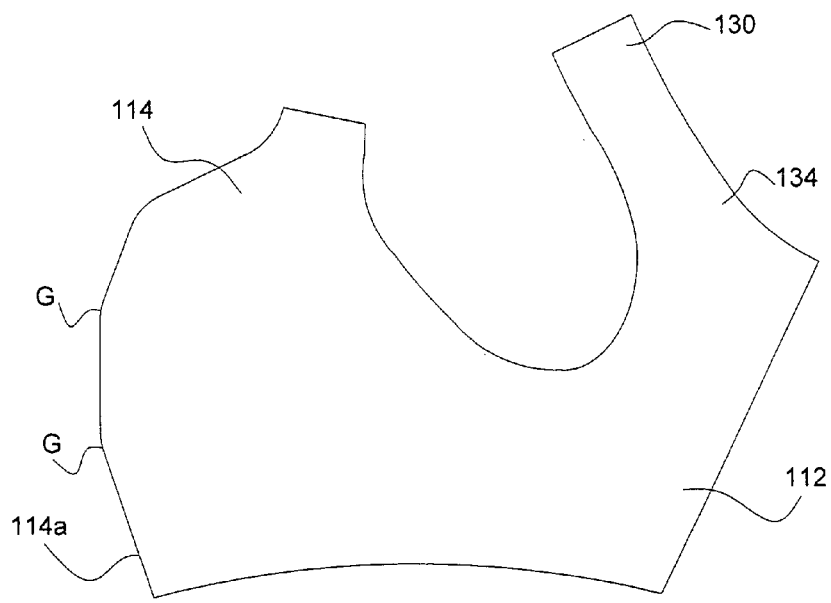
FIG. 3B is an elevational view of a front panel and a side of the back panel prior to finishing and assembly into the garment of FIG. 1, in which the front panel and the side of the back panel are formed unitarily.

FIGS. 3A and 3B illustrate a front panel 114 and a side 112a of the back panel 112 prior to finishing and assembly into the garment 100. The front edge 114a of the front panel 114 is gathered between points G, as discussed hereinafter. In FIG. 3A, the front panel 114 and side 112a of the back panel 112 are formed as separate pieces that are sewn together, while in FIG. 3B, they are formed unitarily.

Figure 4:
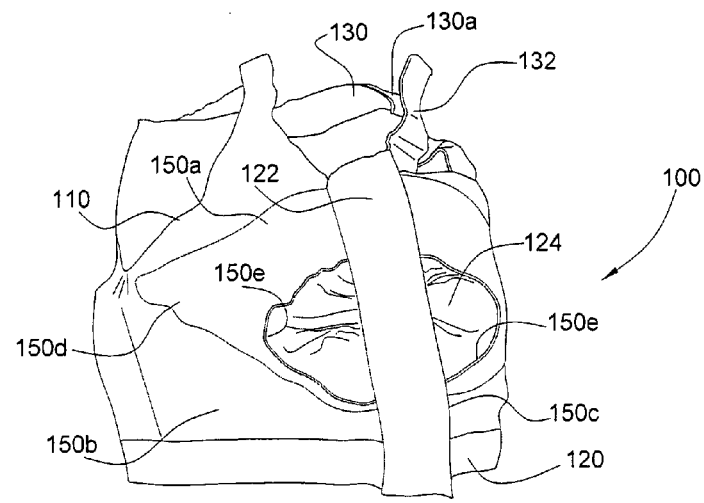
FIG. 4 is an elevational view of the garment of FIG. 1.

As best shown in FIG. 4, the left and right implant stabilizers 150 have top, bottom, front, and back edges 150a-150d, with a cut-out 150e in the front edge 150c that when viewed from the garment front has the approximate shape of an inverted "C" in the left implant stabilizer and a "C" in the right implant stabilizer. The left and right implant stabilizers 150 thus themselves have approximately the shape of an inverted "C" and a "C," respectively, when viewed from the garment front. The cut-out 150e corresponds to the opening of the "C" and inverted "C" shapes and is positioned to permit the areole and surrounding area of the breast to protrude therethrough. The top edges 150a can be contoured so as to be convex over the wearer's breast and concave at the wearer's underarm.

Above and below the cut-outs 150e, the front edges 150c of the left and right implant stabilizers 150 are attached to the front edges of the left and right front panels 114. The bottom and back edges 150b and 150d of the left and right implant stabilizers 150 are attached respectively to the bottom and back edges of the left and right front panels 114. Preferably, each of the left and right implant stabilizers 150 is formed unitarily from a single piece of fabric.

The front edges 114a of the left and right front panels 114 are gathered (at reference number 124) between the upper and lower ends of the cutouts in the implant stabilizers 150.

Figure 5:
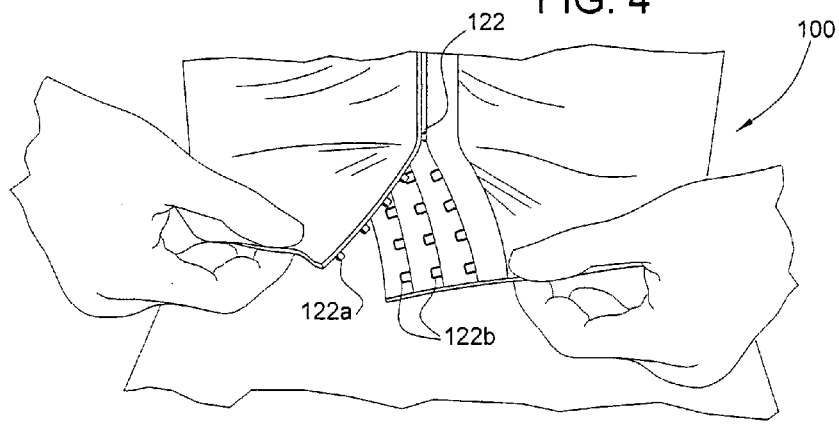
FIG. 5 is a partial front view of the garment of FIG. 1, showing the adjustable front closure.

As best shown in FIG. 5, an adjustable front closure 122 is provided at the front edges 114a of the left and right front panels 114. A typical front closure length is 10 inches.

The front closure 122 is laterally adjustable at its upper end to allow the wearer to tighten or loosen the garment 100 around the mid to upper torso. Also, because the front edges 150c of the implant stabilizers 150 are attached to the front closure 122, when the front closure 122 is laterally adjusted, it functions to increase or decrease the downward pressure applied by the implant stabilizers 150. Preferably, the front closure 122 is a conventional brassiere hook-and-eye type closure that is a plush, shielded, hook-and-eye closure with a single row of hooks 122a and multiple (for example, three) rows of eyes 122b. However, other adjustable closure constructions, including, but not limited to, hook and loop (such as Velcro®) fasteners, are also possible and equally effective.

Figure 2:
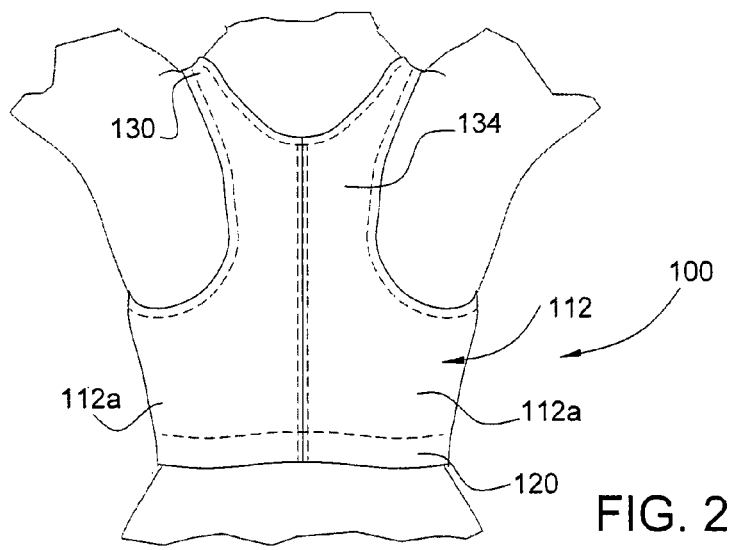
FIG. 2 is a back view of the garment of FIG. 1.
Figure 6:
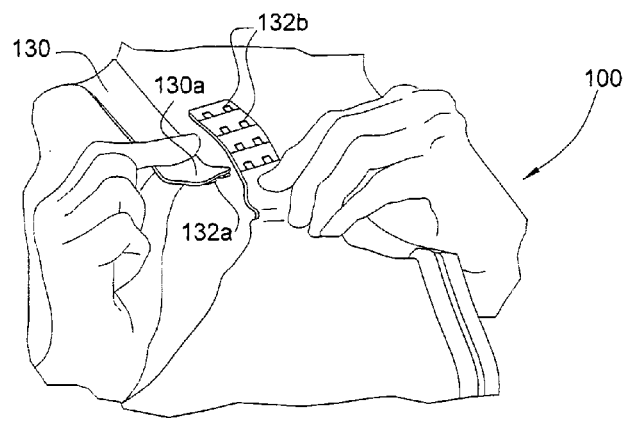
FIG. 6 is a partial side perspective view of the garment of FIG. 1, showing one of the adjustable strap closures.

In the first embodiment shown in FIGS. 1-6, the body 110 also includes left and right adjustable shoulder straps 130 extending from the back panel 112 to the left and right front panels 114, respectively. Preferably, as shown in FIG. 2, the left and right shoulder straps 130 extend from the back panel 112 in a racer back configuration 134 to provide upper back support. Also preferably, as shown in FIG. 6, the left and right shoulder straps 130 are adjustable to provide a better fit of the garment to the wearer. In order to provide adjustment, the shoulder straps 130 can be provided with respective front ends 130a that attach to the left and right front panels 114 via adjustable strap closures 132. Preferably, as best shown in FIGS. 4 and 6, for ease in donning and adjustment, front ends 130a are detachable from the left and right front panels 114, and the strap closures 132 are conventional brassiere hook-and-eye type closures, that is, plush, shielded, hook-and-eye closures with a single row of hooks 132a and multiple rows of eyes 132b. However, other adjustable closure constructions, including, but not limited to, hook and loop (such as Velcro®) fasteners and conventional lingerie strap rings, hooks, and sliders, are also possible and equally effective.

The implant stabilizers 150 apply equal amounts of medium to firm downward and lateral pressure to help muscle tissue relax and accept breast implants in their new position. The upper portion of the implant stabilizers 150 above the cutout section 150e provide downward pressure to prevent upward movement of breast implants, while the side portion of the implant stabilizers 150 to the side of the cutout section 150e provide pressure to prevent lateral movement of implants. The amount of downward and lateral pressure can be increased or decreased by adjusting the position of the front closure 122 to make the body tighter or looser, respectively.

Figure 7:
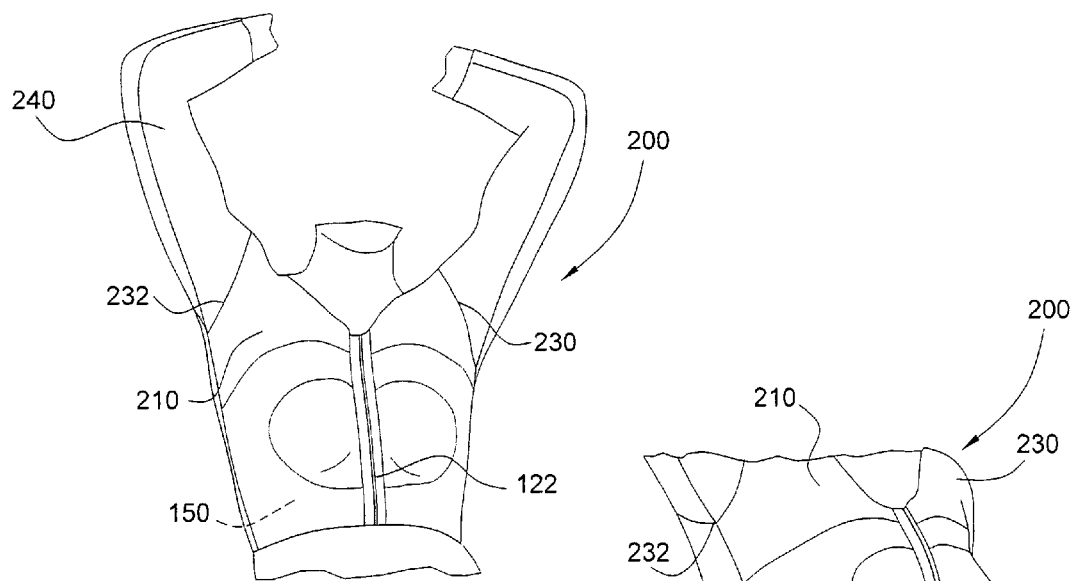
FIG. 7 is a front view of a second embodiment of the garment with breast implant stabilizers in accordance with the invention.
Figure 8:
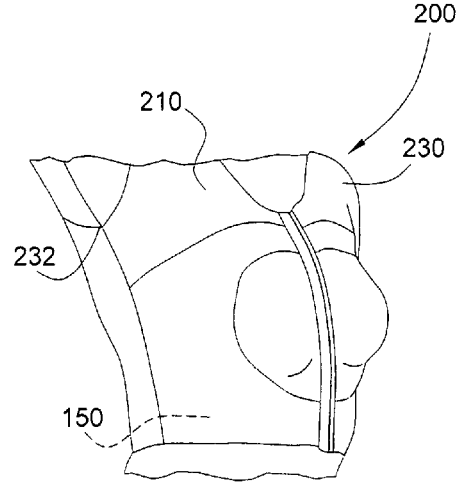
FIG. 8 is a partial side perspective view of the garment of FIG. 7.
Figure 9:
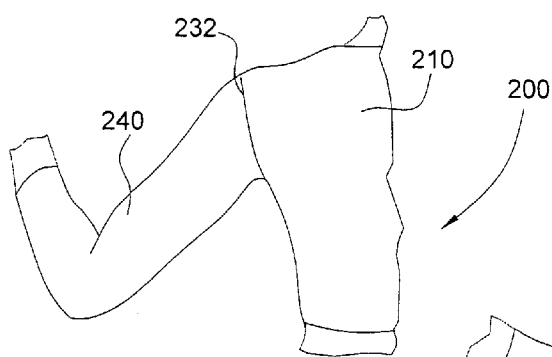
FIG. 9 is a partial back view of the garment of FIG. 7.

With reference to FIGS. 7-9, there is shown a second embodiment 200 of the breast garment in accordance with the present invention, for use when one or more surgical procedures are performed in addition to breast augmentation or reconstruction. The garment 200 includes a body 210 configured in a bolero style (that is, a very short jacket that terminates around the midriff) and left and right built-in implant stabilizers 150. The body 210 is substantially identical to the body 110 of the garment 100, except that the body 210 has non-adjustable full shoulders 230, armholes 232, and sleeves 240 set into the armholes 232, rather than adjustable shoulder straps 130. The implant stabilizers 150 of the garment 200 are substantially identical to those of the garment 100, and are affixed to the inside of the body 210 in the same manner in which the implant stabilizers 150 are affixed to the inside of the body 110.

Figure 10:
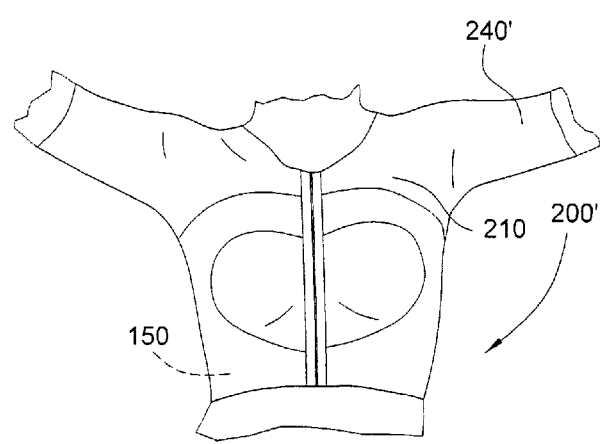
FIG. 10 is a front view of a third embodiment of the garment with breast implant stabilizers in accordance with the invention.

The length of the sleeves 240 depends upon the surgery performed in addition to breast augmentation or reconstruction. Long sleeves 240 as shown in FIGS. 7-9 are used following procedures where upper back, wing, axilla (armpit), shoulder, and arm compression are recommended, for example, following upper back, wing, axilla, arm, shoulder, liposuction, and arm reduction (brachioplasty) procedures. Short sleeves 240', shown in connection with a garment 200' in FIG. 10, are used following procedures where upper back and shoulder compression are recommended, for example, following upper back, wing, axilla, and shoulder liposuction procedures. Other than sleeve length, garment 200' is identical to garment 200.

Figure 11:
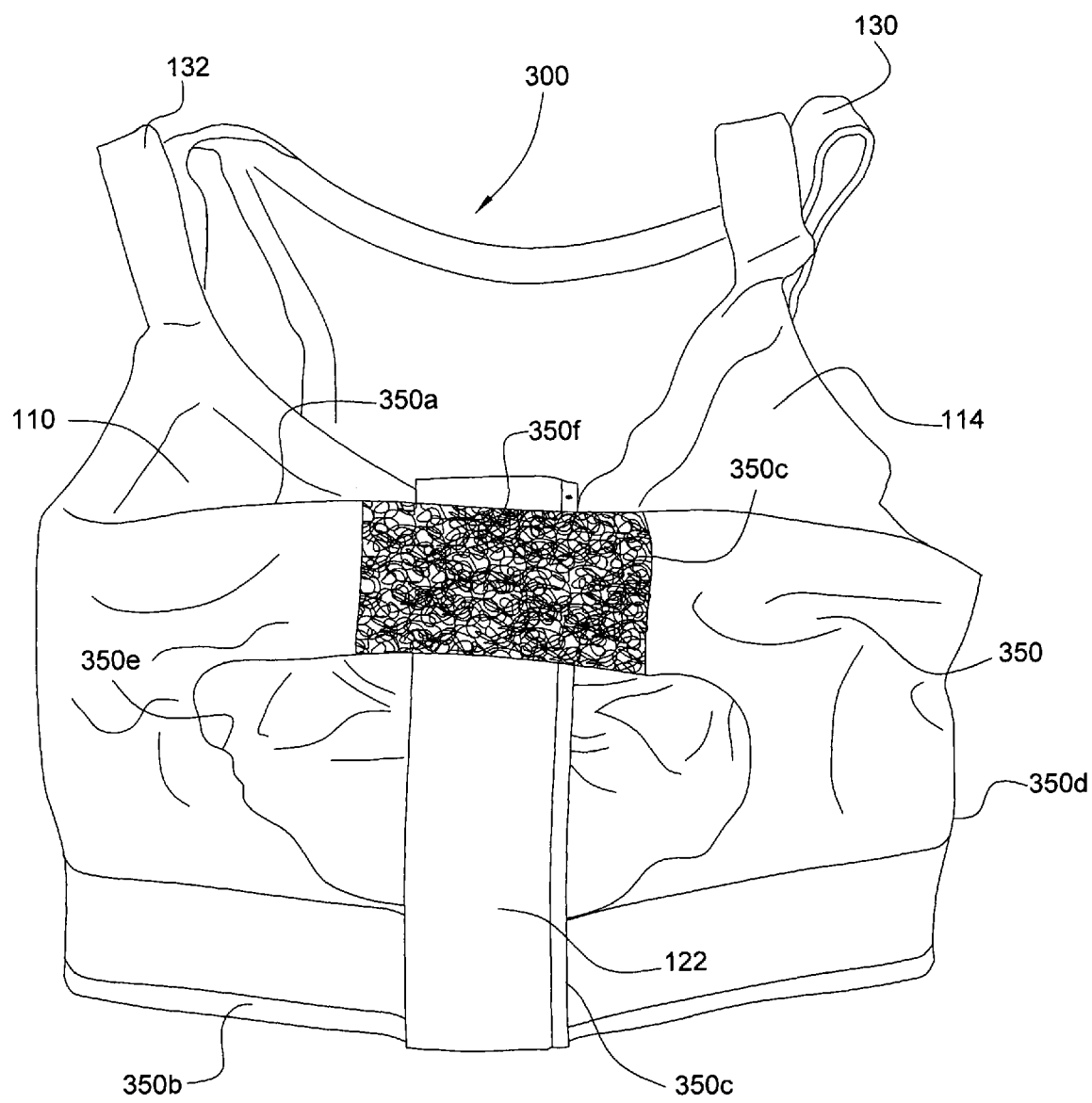
FIG. 11 is a front perspective view of a fourth embodiment of the garment with breast implant stabilizers in accordance with the invention.

With reference to FIG. 11, there is shown a fourth embodiment 300 of the breast garment in accordance with the present invention, for stabilizing breast implants following their surgical placement during breast augmentation or reconstructive procedures. The breast garment 300 comprises a body 110 that is substantially identical to the body 110 of the garment 100, and left and right built-in implant stabilizers 350 (best seen in FIG. 11A) positioned on the outside of the body 110 at the front. The body 110 and the implant stabilizers 350 are both made of a stretch compressive fabric (for example, knitted tricot), preferably in a nylon/lycra blend.

The left and right implant stabilizers 350 have top, bottom, front, and back edges 350a-350d, with a cut-out 350e in the front edge 350c that when viewed from the garment front has the approximate shape of an inverted "C" in the left implant stabilizer and a "C" in the right implant stabilizer. The left and right implant stabilizers 350 thus themselves have approximately the shape of an inverted "C" and a "C," respectively, when viewed from the garment front. The cut-out 350e is positioned to permit the areole and surrounding area of the breast to protrude therethrough. The top edges 350a preferably are contoured so as to be convex over the wearer's breast and concave at the wearer's underarm.

The front edges 350c of the left and right implant stabilizers 350 below the cut-outs 350e are attached respectively to the front edges of the left and right front panels 114. The bottom and back edges 350b and 350d of the left and right implant stabilizers 350 are attached respectively to the bottom and back edges of the left and right front panels 114 and to the front closure 122.

The front edges 350c of the left and right implant stabilizers 350 are provided above the cut-outs 350e with an adjustable, horizontally-extending stabilizer closure 350f. The stabilizer closure 350f preferably is a hook and loop (such as Velcro®) fastener. However, other adjustable closure constructions, including, but not limited to, a conventional brassiere hook-and-eye type closure with a single row of hooks and multiple rows of eyes, are also possible and equally effective. Because the front edges 350c below the cut-outs 350e are attached to the front closure 122, the front closure 122 functions both to tighten or loosen the garment 100 around the mid to upper torso and to adjust the lateral pressure applied by the implant stabilizers 350 at the bottom.

The implant stabilizers 350 apply equal amounts of medium to firm downward and lateral pressure to help muscle tissue relax and accept breast implants in their new position. The upper portion of the implant stabilizers 350 above the cutout section 350e provide downward pressure to prevent upward movement of breast implants, while the side portion of the implant stabilizers 350 to the side of the cutout section 350e provide pressure to prevent lateral movement of implants. The amount of downward and lateral pressure can be increased or decreased by adjusting the position of the stabilizer closure 350f. The stabilizer closure 350f provides a wider range of adjustment than is possible with just the front closure 122 alone.

Figure 12:
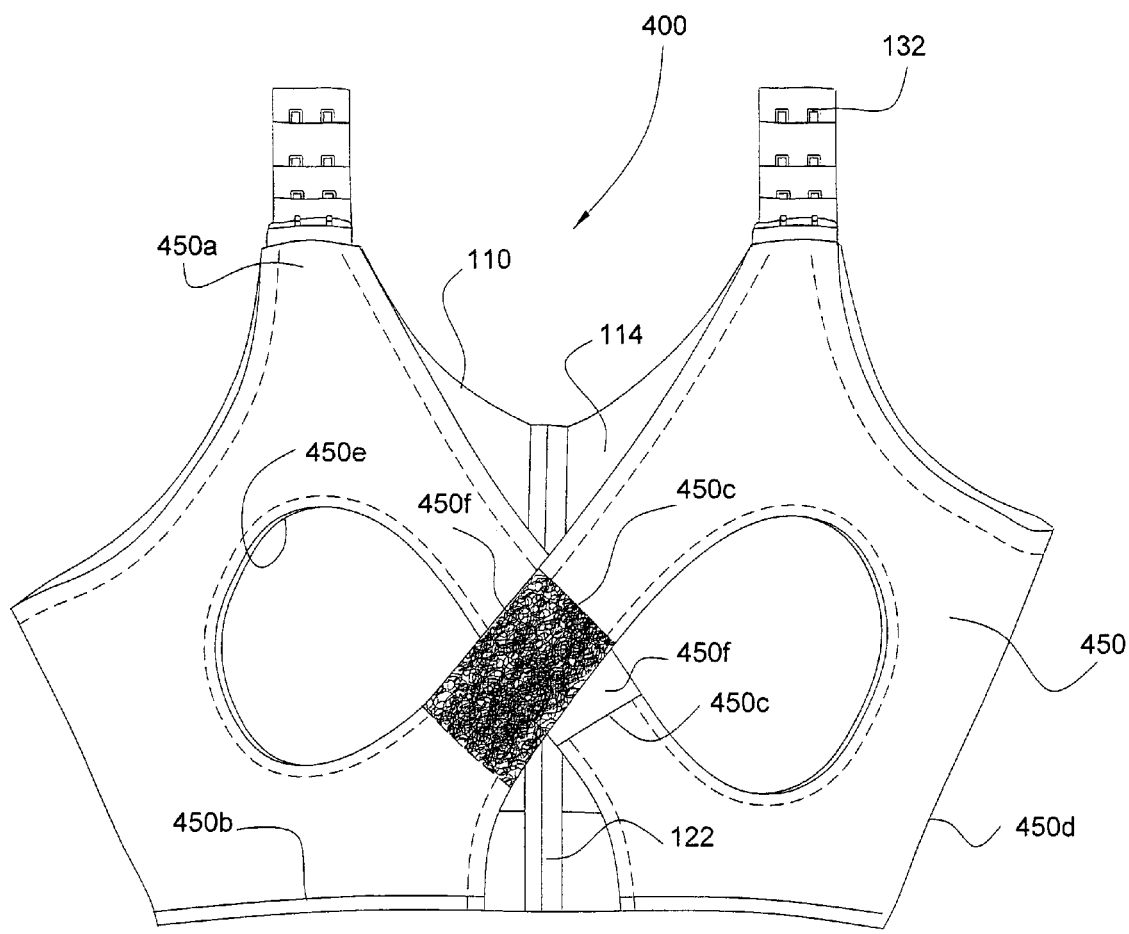
FIG. 12 is a front perspective view of a fifth embodiment of the garment with breast implant stabilizers in accordance with the invention.

With reference to FIG. 12, there is shown a fourth embodiment 400 of the breast garment in accordance with the present invention, for stabilizing breast implants following their surgical placement during breast augmentation or reconstructive procedures. The breast garment 400 comprises a body 110 that is substantially identical to the body 110 of the garment 100, and left and right built-in implant stabilizers 450 positioned on the outside of the body 110 at the front. The body 110 and the implant stabilizers 450 are both made of a stretch compressive fabric (for example, knitted tricot), preferably in a nylon/lycra blend. The body 110 has a front closure 122 that is laterally adjustable at its upper end to allow the wearer to tighten or loosen the garment 100 around the mid to upper torso.

The left and right implant stabilizers 450 have top, bottom, front, and back edges 450a-450d, with a cut-out 450e in the front edge 450c that when viewed from the garment front has the approximate shape of an inverted "C" in the left implant stabilizer and a "C" in the right implant stabilizer. The left and right implant stabilizers 450 thus themselves have approximately the shape of an inverted "C" and a "C," respectively, when viewed from the garment front. The cut-out 450e is positioned to permit the areole and surrounding area of the breast to protrude therethrough. The top edges 450a are attached to the top edges of the left and right front panels 114 in the vicinity of the adjustable strap closures 132, but are otherwise unattached to the body 110, while the back edges 450c are attached to the back edges of the left and right front panels 114. The implant stabilizers 450 preferably are contoured so as to be concave at the wearer's underarm. The front edges 450c of the left and right implant stabilizers 450 below the cut-outs 450e, and the bottom edges 450c, are not attached to the body 110.

The front edges of the left and right implant stabilizers 450 are provided above and below the cut-outs 450e with adjustable, diagonally-extending, left and right stabilizer closures 450f. That is, each stabilizer closure 450f extends from the front edge 450c of one stabilizer 450 above the cut-out 450e to the front edge 450c of the other stabilizer 450 below the cut-out 450e. The stabilizer closures 450f preferably are hook and loop (such as Velcro®) fasteners. However, other adjustable closure constructions, including, but not limited to, a conventional brassiere hook-and-eye type closure with a single row of hooks and multiple rows of eyes, are also possible and equally effective.

The implant stabilizers 450 apply medium to firm downward and lateral pressure to help muscle tissue relax and accept breast implants in their new position. The upper portion of the implant stabilizers 450 above the cutout section 450e provide downward pressure to prevent upward movement of breast implants, while the side portion of the implant stabilizers 450 to the side of the cutout section 450e provide pressure to prevent lateral movement of implants. The amount of downward and lateral pressure can be increased or decreased by adjusting the position of the stabilizer closures 450f. The stabilizer closures 450f provide the capability of applying differential medium to firm downward and lateral pressure to both breasts; that is, a different and adjustable amount of pressure to each breast.

In addition, because the implant stabilizers 450 are attached to the front panels 114 of the body 110 in the vicinity of the adjustable strap closures 132, the adjustable strap closures 132 also are capable of providing differential upward pressure on the breasts.

Figure 13:
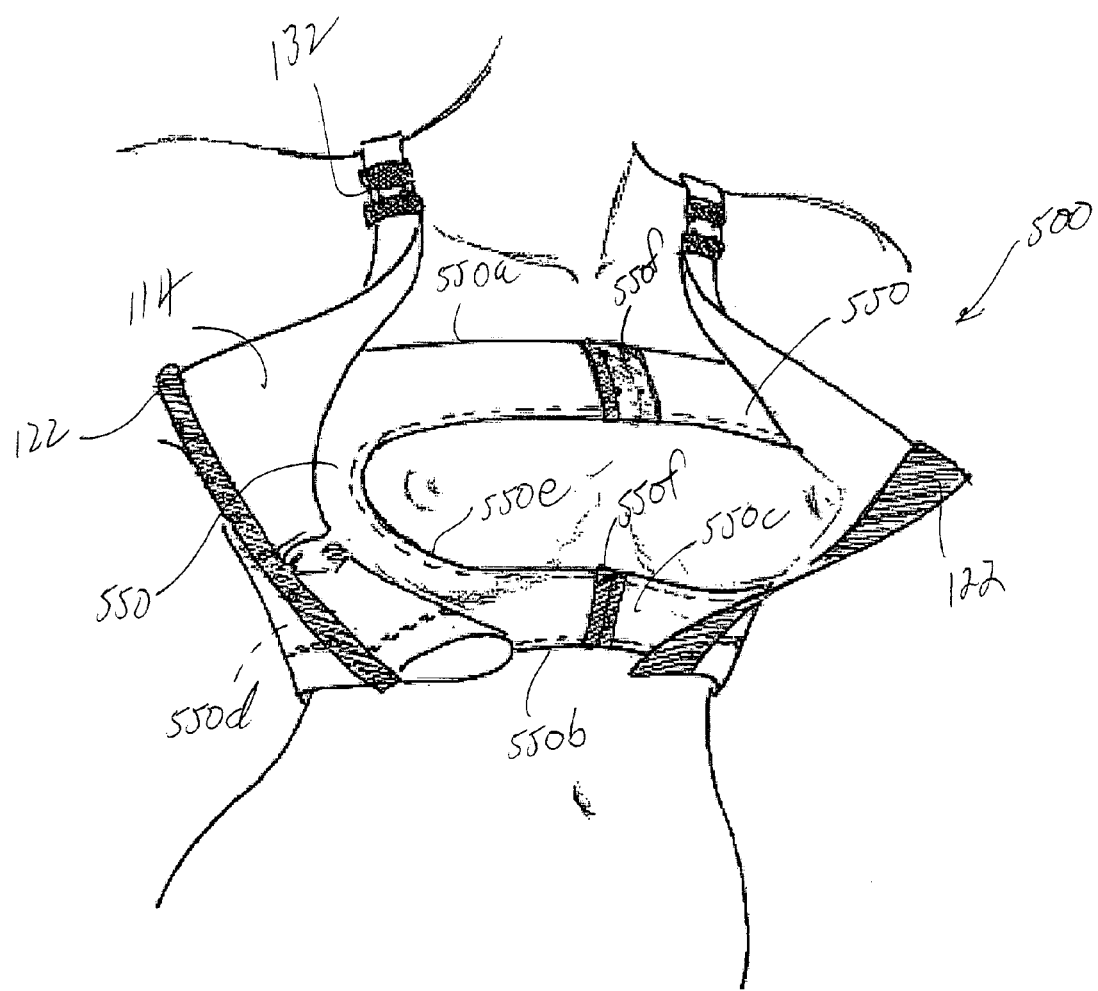
FIG. 13 is a front perspective view of a sixth embodiment of the garment with breast implant stabilizers in accordance with the invention.

With reference to FIG. 13, there is shown a fifth embodiment 500 of the breast garment in accordance with the present invention, for stabilizing breast implants following their surgical placement during breast augmentation or reconstructive procedures. The breast garment 500 comprises a body that is substantially identical to the body 110 of the garment 100, and left and right built-in implant stabilizers 550 positioned on the inside of the body 110 at the front. The body 110 and the implant stabilizers 550 are both made of a stretch compressive fabric (for example, knitted tricot), preferably in a nylon/lycra blend. The body 110 has a front closure 122 that is laterally adjustable to allow the wearer to tighten or loosen the garment 100 around the mid to upper torso.

The left and right implant stabilizers 550 have top, bottom, front, and back edges 550a-550d, with a cut-out 550e in the front edge 550c that when viewed from the garment front has the approximate shape of an inverted "C" in the left implant stabilizer and a "C" in the right implant stabilizer. The left and right implant stabilizers 550 thus themselves have approximately the shape of an inverted "C" and a "C," respectively, when viewed from the garment front. The cut-out 550e corresponds to the opening of the "C" and inverted "C" shapes and is positioned to permit the areole and surrounding area of the breast to protrude therethrough. The back edges 550c are attached to the back edges of the left and right front panels 114. The front edges 550c of the left and right implant stabilizers 550 below the cut-outs 550e, and the bottom edges 550c, are not attached to the body 110.

The front edges of the left and right implant stabilizers 550 are provided above and below the cut-outs 550e with adjustable, laterally-extending, left and right stabilizer closures 550f. The stabilizer closures 550f preferably are a conventional brassiere hook-and-eye type closure with a single row of hooks and multiple rows of eyes. However, other adjustable closure constructions, including, but not limited to, hook and loop (such as Velcro®) fasteners, are also possible and equally effective.

With reference to FIGS. 14A-14C, there is shown a sixth embodiment 600 of the breast garment in accordance with the present invention, for stabilizing breast implants following their surgical placement during breast augmentation or reconstructive procedures. The breast garment 600 comprises a body that is substantially identical to the body 110 of the garment 100, and left and right built-in implant stabilizers 650 positioned on the inside of the body 110 at the front. The body 110 and the implant stabilizers 650 are both made of a stretch compressive fabric (for example, knitted tricot), preferably in a nylon/lycra blend. The body 110 has a front closure 122 that is laterally adjustable to allow the wearer to tighten or loosen the garment 100 around the mid to upper torso.

The left and right implant stabilizers 650 have top, bottom, front, and back edges 650a-650d, with a cut-out 650e in the front edge 650c that when viewed from the garment front has the approximate shape of an inverted "C" in the left implant stabilizer and a "C" in the right implant stabilizer. The left and right implant stabilizers 650 thus themselves have approximately the shape of an inverted "C" and a "C," respectively, when viewed from the garment front. The cut-out 650e corresponds to the opening of the "C" and inverted "C" shapes and is positioned to permit the areole and surrounding area of the breast to protrude therethrough. The top edges 650a are attached to the top edges of the left and right front panels 114 in the vicinity of the adjustable strap closures 132, but are otherwise unattached to the body 110, while the back edges 650c are attached to the back edges of the left and right front panels 114. The front edges 650c of the left and right implant stabilizers 650 below the cut-outs 650e, and the bottom edges 650c, are not attached to the body 110.

The front edges of the left and right implant stabilizers 650 are provided above and below the cut-outs 650e with adjustable left and right stabilizer closures 650f. The stabilizer closures 650f preferably are fastened to each other using hook and loop (such as Velcro®) fasteners.

The lower left and right stabilizer closures 650f extend laterally. The upper left and right stabilizer closures 650f are elastic and of sufficient length that they can be fastened either laterally by attachment to each other, as shown in FIGS. 14A and 14C, or diagonally by attachment to the lower left and right stabilizer closures 650f, as shown in FIG. 14B, so that the left and right implant stabilizers 650 provide adjustable downward, lateral pressure and adjustable breast separation options. One of the upper left and right stabilizer closures 650*f* is formed with inner and outer flaps 651*a* and 651*b*, which receive the other of the upper left and right stabilizer closures 650*f* between them, with the hook and loop fasteners so arranged that the other of the upper left and right stabilizer closures 650*f* is secured between the inner and outer flaps 651*a* and 651*b* when fastened laterally, as shown in FIGS. 14A and 14C. The upper left and right stabilizer closures 650*f* can also be fastened diagonally as shown in FIG. 14B. When the stabilizer closures 650*f* are fastened diagonally, they provide individual implant stability, breast separation or left and right breast adjustments. The upper adjustable stabilizer closures 650*f* provides medium to firm downward pressure, preventing upward movement of breast implants. The lower adjustable stabilizer closures 650*f* provides medium to firm pressure, preventing lateral movement of implants.

With reference to FIGS. 15A-15C, there is shown a seventh embodiment 700 of the breast garment in accordance with the present invention, for stabilizing breast implants following combination upper body liposuction and breast augmentation post-operative procedures. The breast garment 700 comprises a body that is substantially identical to the body 210 of the garment 200, and left and right built-in implant stabilizers 750 positioned on the inside of the body 210 at the front. The implant stabilizers 750 are substantially identical to the implant stabilizers 650 described above with respect to FIGS. 14A and 14B, with top, bottom, front, and back edges 750*a*-750*d*, with cut-outs 750*e* in the front edges 750*c*.

The front edges of the left and right implant stabilizers 750 are provided above and below the cut-outs 750*e* with adjustable left and right stabilizer closures 750*f* substantially identical to the adjustable left and right stabilizer closures 650*f* described above with respect to FIGS. 14A and 14B.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

What is claimed is:

1. A breast garment for stabilizing breast implants following their surgical placement during breast augmentation or reconstructive procedures, comprising:
    a body surrounding the wearer's mid to upper torso, wherein the body has a back panel, a front, a bottom edge, and an inside facing the wearer's mid to upper torso, and wherein:
        the back panel has left and right sides;
        the front has left and right front panels extend forwardly from the left and right sides of the back panel, the left and right front panels having respective, opposing front edges, respective back edges, and respective bottom edges, and
        the body is made of a stretch compressive fabric;
    an elastic band at the bottom edge of the body for providing proper fit around the wearer's midriff;
    left and right built-in implant stabilizers separate from the body and positioned at the front of the body, wherein the left and right built-in implant stabilizers are made of a stretch compressive fabric for applying medium to firm downward and lateral pressure on a wearer's breasts to help muscle tissue relax and accept breast implants in their new position, for providing downward pressure on a wearer's breasts to prevent upward movement of breast implants, and for providing lateral pressure on a wearer's breasts to prevent lateral movement of implants, and wherein the left and right built-in implant stabilizers have top, bottom, front, and back edges, with a cut-out in the front edge shaped to permit the areole and surrounding area of the breast to protrude therethrough; and
    adjusting means for adjusting the amount of downward and lateral pressure applied on the wearer's breasts by the left and right built-in implant stabilizers.

2. A breast garment for stabilizing breast implants following their surgical placement during breast augmentation or reconstructive procedures, comprising:
    a body surrounding the wearer's mid to upper torso, wherein the body has a back panel, a front, a bottom edge, and an inside facing the wearer's mid to upper torso, and wherein:
        the back panel has left and right sides;
        the front has left and right front panels extend forwardly from the left and right sides of the back panel, the left and right front panels having respective, opposing front edges, respective back edges, and respective bottom edges, and
        the body is made of a stretch compressive fabric;
    an elastic band at the bottom edge of the body for providing proper fit around the wearer's midriff;
    left and right built-in implant stabilizers separate from the body and positioned at the front of the body, wherein the left and right built-in implant stabilizers are made of a stretch compressive fabric for applying medium to firm downward and lateral pressure on a wearer's breasts to help muscle tissue relax and accept breast implants in their new position, for providing downward pressure on a wearer's breasts to prevent upward movement of breast implants, and for providing lateral pressure on a wearer's breasts to prevent lateral movement of implants, and wherein the left and right built-in implant stabilizers are located on the inside body the body; and
    adjusting means for adjusting the amount of downward and lateral pressure applied on the wearer's breasts by the left and right built-in implant stabilizers.

3. The breast garment of claim 1, wherein the front edges, back edges, and bottom edges of the left and right built-in implant stabilizers are attached respectively to the opposing front edges, back edges, and bottom edges of the left and right front panels.

4. The breast garment of claim 1, wherein the left and right built-in implant stabilizers are located on the outside of the body.

5. The breast garment of claim 1, wherein the left and right built-in implant stabilizers are located on the inside of the body and wherein at least the back edges of the left and right built-in implant stabilizers are attached respectively to back edges of the left and right front panels; and
    wherein the adjusting means are provided on the left and right built-in implant stabilizers.

6. The breast garment of claim 5, wherein the adjusting means functions to apply the same amount of downward and lateral pressure on both breasts.

7. The breast garment of claim 6, wherein the adjusting means comprises an adjustable, horizontally-extending stabilizer closure provided at the front edges of the left and right built-in implant stabilizers above the cutouts.

8. The breast garment of claim 5, wherein the adjusting means permits the application of a different amount of downward and lateral pressure to each breast.

9. The breast garment of claim 5, wherein the adjusting means comprises adjustable, diagonally-extending, left and right stabilizer closures provided at the front edges of the left and right built-in implant stabilizers above and below the cut-outs.

10. The breast garment of claim 1, wherein the adjusting means comprises adjustable, left and right stabilizer closures provided at the front edges of the left and right built-in implant stabilizers above and below the cut-outs, the left and right stabilizer closures below the cut-outs being elastic and of sufficient length to be fastened laterally to each other, and the left and right stabilizer closures above the cut-outs being elastic and of sufficient length to be fastened laterally to each other as well as fastened diagonally to the left and right stabilizer closures below the cut-outs.

11. The breast garment of claim 1, wherein the adjusting means also performs the function of adjusting the tightness of the garment around the mid to upper torso of the wearer.

12. The breast garment of claim 1, wherein the body and the adjusting means are made of a nylon/spandex blend.

13. The breast garment of claim 1, wherein the cut-out in the left and right built-in implant stabilizers, when viewed from the garment front has the approximate shape of an inverted "C" in the left implant stabilizer and a "C" in the right built-in implant stabilizer.

14. The breast garment of claim 1, wherein each of the left and right built-in implant stabilizers is formed unitarily from a single piece of fabric.

15. The breast garment of claim 1, wherein the cutouts in the left and right built-in implant stabilizers have upper and lower ends, and wherein the front edges of the left and right front panels are gathered between the upper and lower ends of the cutouts.

16. The breast garment of claim 3, wherein the adjusting means comprises an adjustable front closure provided at the opposing front edges of the left and right front panels, wherein the front closure has upper and lower ends and is laterally adjustable at its upper end to allow the wearer to tighten or loosen the garment around the mid to upper torso, in order to increase or decrease the downward pressure applied by the left and right built-in implant stabilizers, and is laterally adjustable at its lower end to allow the wearer to tighten or loosen the garment around the mid to upper torso, in order to increase or decrease the lateral pressure applied by the left and right built-in implant stabilizers.

17. The breast garment of claim 16, wherein the front closure is a brassiere hook-and-eye closure with a single row of hooks and multiple rows of eyes.

18. The breast garment of claim 16, wherein the front closure comprises hook and loop fasteners.

19. The breast garment of claim 1, further comprising left and right adjustable shoulder straps extending from the back panel of the body to the left and right front panels, respectively, of the body.

20. The breast garment of claim 19, wherein the left and right shoulder straps extend from the back panel in a racer back configuration to provide upper back support.

21. The breast garment of claim 19, wherein the shoulder straps are provided with respective front ends that attach to the left and right front panels via adjustable strap closures.

22. The breast garment of claim 21, wherein the front ends of the shoulder straps are detachable from the left and right front panels for ease in donning and adjustment.

23. The breast garment of claim 1, wherein the body is configured in a bolero style and has non-adjustable full shoulders, armholes, and sleeves set into the armholes.

24. The breast garment of claim 1, further comprising a laterally adjustable front closure provided at the front edges of the left and right front panels for providing proper fit around the mid to upper torso.

25. The breast garment of claim 2, further comprising a laterally adjustable front closure provided at the front edges of the left and right front panels for providing proper fit around the mid to upper torso.

26. A breast garment comprising:
a body surrounding the wearer's mid to upper torso, wherein the body has a back panel, a front, a bottom edge, and an inside facing the wearer's mid to upper torso, and wherein:
the back panel has left and right sides;
the front has left and right front panels extend forwardly from the left and right sides of the back panel, the left and right front panels having respective, opposing front edges, respective back edges, and respective bottom edges, and
the body is made of a stretch compressive fabric;
an elastic band at the bottom edge of the body for providing proper fit around the wearer's midriff;
left and right built-in stabilizers separate from the body and positioned at the front of the body, wherein the left and right built-in stabilizers are made of a stretch compressive fabric for applying medium to firm downward and lateral pressure on a wearer's breasts, for providing downward pressure on a wearer's breasts, and for providing lateral pressure on a wearer's breasts, and wherein the left and right built-in stabilizers have top, bottom, front, and back edges, with a cut-out in the front edge shaped to permit the areole and surrounding area of the breast to protrude therethrough; and
adjusting means for adjusting the amount of downward and lateral pressure applied on the wearer's breasts by the left and right built-in stabilizers.

27. The breast garment of claim 26, further comprising a laterally adjustable front closure provided at the front edges of the left and right front panels for providing proper fit around the mid to upper torso.

28. A breast garment comprising:
a body surrounding the wearer's mid to upper torso, wherein the body has a back panel, a front, a bottom edge, and an inside facing the wearer's mid to upper torso, and wherein:
the back panel has left and right sides;
the front has left and right front panels extend forwardly from the left and right sides of the back panel, the left and right front panels having respective, opposing front edges, respective back edges, and respective bottom edges, and
the body is made of a stretch compressive fabric;
an elastic band at the bottom edge of the body for providing proper fit around the wearer's midriff;
left and right built-in stabilizers separate from the body and positioned at the front of the body, wherein the left and right built-in stabilizers are made of a stretch compressive fabric for applying medium to firm downward and lateral pressure on a wearer's breasts, for providing downward pressure on a wearer's breasts, and for providing lateral pressure on a wearer's breasts, and wherein the left and right built-in stabilizers are located on the inside of the body; and
adjusting means for adjusting the amount of downward and lateral pressure applied on the wearer's breasts by the left and right built-in stabilizers.

29. The breast garment of claim 28, further comprising a laterally adjustable front closure provided at the front edges of the left and right front panels for providing proper fit around the mid to upper torso.

* * * * *